(12) United States Patent
Mischi (10) Patent No.: US 9,141,766 B2
(45) Date of Patent: Sep. 22, 2015

(54) PERFUSION SCANNING DETECTS ANGIOGENESIS FROM SIMILARITY IN EVOLUTION OF LOCAL CONCENTRATIONS OF CONTRAST AGENT

(75) Inventor: Massimo Mischi, Eindhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 50 days.

(21) Appl. No.: 13/876,355

(22) PCT Filed: Sep. 27, 2011

(86) PCT No.: PCT/EP2011/066709
§ 371 (c)(1),
(2), (4) Date: Mar. 27, 2013

(87) PCT Pub. No.: WO2012/041822
PCT Pub. Date: Apr. 5, 2012

(65) Prior Publication Data
US 2013/0182933 A1    Jul. 18, 2013

Related U.S. Application Data

(60) Provisional application No. PCT/EP2011/066709, filed on Sep. 27, 2011.

(30) Foreign Application Priority Data

Sep. 28, 2010  (EP) .................................... 10180866

(51) Int. Cl.
G06F 19/00         (2011.01)

(52) U.S. Cl.
CPC .............. G06F 19/36 (2013.01); G06F 19/321 (2013.01); *G06F 19/3468* (2013.01)

(58) Field of Classification Search
None
See application file for complete search history.

(56) References Cited

U.S. PATENT DOCUMENTS

| 6,512,807 | B1 | 1/2003 | Pohlman et al. | |
|---|---|---|---|---|
| 7,774,041 | B2 * | 8/2010 | Nambu et al. | 600/407 |
| 7,826,885 | B2 * | 11/2010 | Nambu et al. | 600/407 |
| 8,509,507 | B2 * | 8/2013 | Meetz et al. | 382/128 |
| 2003/0097076 | A1 * | 5/2003 | Nambu et al. | 600/504 |
| 2010/0067767 | A1 | 3/2010 | Arakita et al. | |

FOREIGN PATENT DOCUMENTS

WO     WO 00/15107     3/2000

OTHER PUBLICATIONS

International Search Report for PCT/EP2011/066709, mailed Jun. 18, 2012.

(Continued)

*Primary Examiner* — Tsung-Yin Tsai
(74) *Attorney, Agent, or Firm* — Nixon & Vanderhye P.C.

(57) ABSTRACT

The invention relates to using a perfusion scanning medical imaging technique to generate an image of a perfusable structure of an organism. A fluid is flowing through the structure, and a dose of a traceable agent is present in the fluid. The evolution of the spatial concentration of the agent, e.g., a set of values of the magnitude of the concentration assumed at various moments over a period of time, is determined for a plurality of locations within the structure. The spatial pattern of the evolutions is analyzed and an image is generated on the basis of this analysis in order to enable the medical practitioner to draw conclusions about the dispersion characteristics of the perfusable structure.

8 Claims, 6 Drawing Sheets

(56) References Cited

OTHER PUBLICATIONS

Written Opinion of the International Searching Authority for PCT/EP2011/066709, mailed Jun. 18, 2012.
Wang, Z. et al., "Best Neighborhood Matching: An Information Loss restoration Technique for Block-Based Image Coding Systems", IEEE Transactions on Image Processing, vol. 7, No. 7, (1998), pp. 1056-1061.
Gravel, P. et al., "A Method for Modeling Noise in Medical Images", IEEE Transactions on Medical Imaging, vol. 23, No. 10, (Oct. 2004), pp. 1221-1232.
Hart, D.P., "The Elimination of Correlation Errors in PIV Processing", $9^{th}$ Int'l. Symp. on Appl. of Laser Techniques to Fluid Mechanics, (Jul. 1998), p. 8PP.

\* cited by examiner

PERFUSION SCANNING DETECTS ANGIOGENESIS FROM SIMILARITY IN EVOLUTION OF LOCAL CONCENTRATIONS OF CONTRAST AGENT

This application is the U.S. national phase of International Application No. PCT/EP2011/066709, filed 27 Sep. 2011, which designated the U.S. and claims priority to EP Application No. 10180866.5, filed 28 Sep. 2010, the entire contents of each of which are hereby incorporated by reference.

FIELD OF THE INVENTION

The invention relates to a method of controlling generating an image of a perfusable structure of an organism, while a fluid is flowing through the perfusable structure. The invention further relates to a system for controlling generating such image and to control software on a computer-readable medium.

BACKGROUND ART

A perfusable structure is a structure that enables the passage of a fluid (e.g., a liquid or a gas) through the structure. An example of a perfusable structure is the vascular structure of an organ of an organism (plant, animal, human), such as the vascular structure of the brains or heart of a human or of an animal, or the vascular structure of a gland, e.g., the prostate of a male mammal. Medical imaging techniques based on monitoring the perfusion of a fluid (lymph) through the vessels of a lymphatic system or blood through the blood vessels to an organ or to a tissue are commonly referred to as "perfusion scanning techniques".

Examples of such perfusion scanning medical imaging techniques are computed tomography (CT) perfusion, magnetic resonance imaging (MRI) perfusion, nuclear medicine (NM) perfusion, ultrasound perfusion imaging, etc.

In CT perfusion imaging, a traceable iodine-containing contrast agent is injected into the blood of a patient. The contrast agent is transported along the vascular system of the patient. As the contrast agent absorbs the X-rays, the dispersion of the contrast agent can be determined, revealing how much blood is preset and how fast the blood is moving by measuring the vascular transit time.

In MR perfusion imaging, a traceable paramagnetic agent is injected into the vascular structure at a certain location, and the agent's dispersion is monitored as the agent's presence changes the relaxivity of the blood plasma in response to an RF (radio frequency) electromagnetic stimulus. Within this context, the term "relaxivity" refers to the ability of the magnetic compounds of the traceable agent to alter the relaxation times of the blood plasma.

In NM perfusion imaging, the traceable agent is a dose of a radioactive material (also referred to as a "radiopharmaceutical" or "radiotracer") that is introduced into the blood of a patient. The radiation of the radioactive material is detected and provides information about the material's location and dispersion.

In ultrasound perfusion imaging, the traceable agent comprises gas-filed microbubbles that are administered intravenously. Microbubbles are configured to backscatter ultrasound waves to a much higher degree than the surrounding tissue of the body. The backscattered ultrasound waves contain information about the acoustic properties of the structure being investigated and, therefore, about the location of the microbubbles. Doppler-effect measurements provide information about the flow rate (velocity) of the blood. Power-Doppler measurements provide information on blood volume fraction (i.e., the volume of blood in the tissue relative to the total volume of the tissue).

The perfusion-based imaging techniques enable to infer characteristics of the vascular system of a patient from the dispersion of the traceable agent, e.g., the detection of angiogenesis (the development of new blood vessels). As well known, angiogenesis plays an important role in the growth and metastasis of tumors.

SUMMARY OF THE INVENTION

A problem recognized by the inventor is that the known applications of the perfusion imaging techniques cannot readily characterize the perfusable structure, e.g., the tissue microvasculature, at dimensions that are smaller than the imaging resolution. For example, there is a lower limit to the dimensions of the features of a tumor that a medical expert can recognize in an image obtained through a perfusion-based imaging technique. Currently, the detection of tumor microvascular growth and the diagnosis for cancer require that samples of a tissue be obtained by means of invasive biopsy procedures. It is an object of the invention, therefore, to enable non-invasive detection of tumor microvascular growth using a perfusion-based imaging technique.

The inventor proposes a method of controlling generating an image of a perfusable structure of an organism, e.g., a piece of the tissue of an organ of the human body. The image is generated, e.g., on a display monitor or via a printer. A fluid is flowing through the perfusable structure, and a dose of a traceable agent is present in the fluid flowing through the perfusable structure. In the human body the fluid is, e.g., the blood flowing through the microvasculature, and the traceable agent is, e.g., a dose of a substance that is provided through an intravenous injection and that is traceable from outside the human body. The method comprises following steps. For each specific one of a plurality of locations in the perfusable structure, the method comprises following steps. A further quantity is determined dependent on multiple evolutions of a physical quantity, representative of a spatial concentration of the traceable agent, e.g., the amount of the traceable agent per unit volume. Each respective one of the multiple further evolutions is determined for a respective one of multiple further ones of the plurality of locations in a specific neighborhood of the specific location. A specific indicator is allocated to the specific location in dependence on the further quantity for control of representing the specific location in the image.

The concept "evolution of the physical quantity" as used above refers to the development of the physical quantity over time, or a temporal characteristic of the physical quantity, or a temporal pattern of change in a magnitude or other descriptive attribute of the physical quantity. For example, the physical quantity is the magnitude of the spatial density or spatial concentration (scalar) of the traceable agent monitored at the plurality of locations. The evolution of the magnitude as monitored at a particular location may be characterized by a course wherein the magnitude remains substantially nil until the magnitude starts to increase at a first time T1, reaches a maximum at a second time T2, stays substantially at the maximum until a third time T3 and then decreases until the magnitude drops to substantially nil at a fourth time T4. As another example, the physical quantity is the gradient (vector) of the density of the traceable agent whose temporal behavior is monitored at the plurality of locations. Still other examples of the physical quantity that may be used include the gradient of the spatial density or spatial concentration at the particular location; the first-order time derivative of the spatial concentration at the particular location; a combination of the first-order time derivative of the spatial concentration at the particular location and one or more higher-order time derivatives of the spatial concentration at the particular location; the first-order time derivative of the gradient of the spatial concentration at the particular location, a combination of the first-order time derivative of the gradient of the spatial concentration at the particular location and one or more higher-order time derivatives of the gradient at the particular location, etc., or another weighted combination of two or more of the entities being mentioned above as examples of the physical quantity.

The evolution may be quantified by a sequence of samples of the physical quantity as monitored at the particular location, each next sample being representative of an attribute (e.g., magnitude) of the physical quantity at the next sampling time. Alternatively, the evolution may be quantified by one or more parameters extracted from such sequence: e.g., the maximum magnitude of the physical quantity, the amplitudes of the Fourier components of the sequence that have the higher energy contents, a measure of the width of a graph representing the sequence on the time axis, etc.

The image is, e.g., a 2-dimensional image or a 3-dimensional image. Alternatively, the image is a 1-dimensional image, e.g., a graph representing the distribution of similarity values along a cross-section of a 2-dimensional topography of similarity values.

As mentioned above, a dose of a traceable agent is present in the fluid flowing through the perfusable structure. The traceable agent is present in the fluid as a result of the traceable agent having been introduced into the fluid from an external source, e.g., the traceable agent has been injected into the fluid. Alternatively, the presence of the traceable agent in the fluid is a result of the traceable agent having been generated within the fluid in response to an external stimulus. For example, a high-energy burst of ultrasound may produce microbubbles by means of cavitation, i.e., without the need for introducing the microbubbles from an external source.

The invention is based on the insight that the evolution (i.e., the dynamics) of the dispersion of the traceable agent as monitored at different locations throughout the perfusable structure using a perfusion-based imaging technique, allows drawing conclusions about the character of the perfusable structure.

In an embodiment of the method, the method comprises determining a specific evolution of the physical quantity at the specific location. The further quantity is then representative of a degree of similarity of the specific evolution to the multiple further evolutions. For example, the further quantity is representative of, e.g., a degree of similarity between the specific evolution and an average of the multiple further evolutions. As another example, the further quantity is a mathematical function, e.g., the average, or the mode or the median of respective degrees of similarity between the specific evolution and respective ones of the further evolutions.

A degree of similarity can be quantified by determining some sort of interdependence of the entities to be interrelated, e.g., the evolution at the specific location on the one hand and the average of the multiple further evolutions in the neighborhood on the other hand, or the specific evolution on the one hand and a respective one of the multiple further evolutions on the other hand. For example, a measure of similarity is based on a magnitude of a difference between the specific evolution and, e.g., an average of the multiple further evolutions. The specific evolution defines a first sequence of a predetermined number of first values of the magnitude of the concentration of the traceable agent, different ones of the first values in the first sequence being associated with different sampling times. Likewise the average of the multiple further evolutions defines a second sequence of the same predetermined number of second values. The difference between the specific evolution and the average of the multiple further evolutions expressed in a certain parameter domain, for example, the time domain or the frequency domain, is then a third sequence of third values. The similarity measure is then, for example, the total of the sum of the third values. As another example, similarity is determined on the basis of coherence, correlation, or entropy (information content) of the graphs that represent the evolution at neighboring locations. As known in the field of statistical time-series analysis or spectral analysis, coherence is a mathematical concept for describing the strength of association between a pair of such series, where the possible dependence between the two series does not have to be based on simultaneity of the occurring values, but may be based on time-shifted (leading or lagging) or smoothed relationships between the values of the two series. Correlation is a mathematical concept that refers to any of a broad class of statistical relationships between observed data values. Entropy is a mathematical concept that refers to a degree of deviation from predictability for the next sample in a time series, given the preceding samples and time of occurrence. A time series can therefore be assigned a value representative of its entropy content. Two time series, i.e., the evolution at the specific location and the locally averaged evolution, could be compared on the basis of their entropy. For a discussion of algorithms to determine interdependence see, e.g., "Performance of different synchronization measures in real data: A case study on electroencephalographic signals", R. Quian Quiroga et al., Physical Review E, Volume 65, pp. 041903-1—041903-14, published Mar. 15, 2002, and "From EEG signals to brain connectivity: A model-based evaluation of interdependence measures", F. Wendlinga et al., Journal of Neuroscience methods, Vol. 183, pp. 9-18, 2009, and the literature references included in these papers.

A higher degree of similarity between, for example, the evolution monitored at a specific location and a measure of the evolution monitored at a neighboring locations may correspond to a higher rate of diffusion (intravascular dispersion dynamics) of the traceable agent and, therefore, to a denser network of blood vessels. However, as convection may play a relevant role as well, the degree of similarity may also correlate with the ratio of the transport of the traceable agent by means of convection and the transport of the traceable agent through dispersion. This ratio is sometimes characterized in the literature by a dimensionless fluid dynamic number referred to as the Péclet number. The Péclet number is defined as the ratio of the rate of advection of a physical quantity by the flow (referred to above as "convection") to the rate of diffusion of the same physical quantity driven by an appropriate gradient. The Péclet number is also correlated with the intravascular hemodynamic characteristics that also depend on the vascular architecture see, e.g., Sheppard C. W., "Basic principles of tracer methods: Introduction to mathematical tracer kinetics", 1962, London, Wiley.

An average of the multiple further evolutions is, for example, the evolution locally averaged over the neighborhood of the specific location. The averaged evolution is then represented by a time series of averaged samples, each respective one thereof being the average of the samples of the further evolutions associated with the respective time.

The average may be a uniform average, wherein the further evolutions are given equal weights, e.g., unity. Alternatively, the average may be a weighted average, wherein different ones of the multiple further evolutions are given different weighting factors when determining the locally averaged evolution. As an option, the magnitudes of the weighting factors are programmable in advance. In an example scenario, the programmability of the weighting factors enables to use any shape of neighborhood by means of selectively setting the weighting factors to zero or unity for the further evolutions. In another scenario, the programmability of the weighting factors also enables to gradually change the contributions of the further evolutions to the eventual average, with distance from the specific location by means of gradually changing the magnitudes of the weighting factors, for example, from unity to zero, when the distance increases. In yet another scenario, the programmability of the weighting factors can be used to test different distributions of the weighting factors in order to determine an optimum or near-optimum, given the structure being examined. As another example, the further quantity is an average of respective similarities of the specific evolution to respective ones of the multiple further evolutions. Again, the average may be a weighted average, wherein different ones of the similarities are taken into account in determining the average after the different similarities have been given different weighting factors. Optionally, the magnitudes of the weighting factors are programmable in advance.

The concepts "average", "median" and "mode", referred to above, are examples of the mathematical function of the respective degrees of similarity between the specific evolution and respective ones of the further evolutions. These concepts are well known in the field of statistics and probability theory. Other mathematical functions may be used to process the degrees of similarity. Again, weighting factors may be taken into account to bias the outcome of the mathematical function.

The degree of diffusion (and therefore similarity) can be associated with the underlying microvascular structure and can be used to characterize the presence of angiogenesis. This, in turn, can be related to the presence of cancer or other forms of tissue inflammation. More in general, a method according to the invention could also be used to characterize different media and materials, other than tissue, where an indicator (i.e., a traceable agent) can pass through.

Note that the degree of similarity depends on the algorithm used, as well as on the adopted weights and mathematical function. Different algorithms to determine coherence may give different degrees of similarity given the same evolutions in the neighborhood. Different algorithms to determine correlation may give different degrees of similarity given the same evolutions in the neighborhood. Different algorithms to determine a difference in entropy content may give different degrees of similarity given the same evolutions in the neighborhood. An algorithm to determine coherence may give a degree of similarity that is different from the degree of similarity determined using an algorithm to determine differences in entropy content. Therefore, the degree of similarity may be determined by combining, averaging or otherwise weighing the different outcomes of different algorithms. For example, consider the approach wherein multiple similarity outcomes are determined for a specific location using multiple different algorithms. Assume further that the degree of similarity to be eventually used for the specific location is taken as an average of the similarity outcomes. If the similarity outcomes are very much alike to each other according to some pre-determined criterion, the average of the similarity outcomes will be close to each of the similarity outcomes. However, if the similarity outcomes are not in agreement with each other by far, according to the pre-determined criterion, the average of the similarity outcomes will be toned down somewhat with respect to the higher one of the similarity outcomes. As an option, the average is a weighted average depending on the spread among the similarity outcomes. Alternatively, one could determine a ratio (or a weighted ratio) of similarity outcomes obtained by a pair of different algorithms for the same specific location, and map the ratio onto the specific indicator associated with the specific location. As yet another option, different degrees of similarity obtained for the same specific location through different algorithms could be processed as an array of similarity values to be mapped onto the indicator via, e.g., an artificial neural network. As known, an artificial neural network is a signal processing tool that can be configured, automatically through training, in order to implement a complicated relationship between input and output, e.g., as a classifier that maps different inputs to a specific output, the later being representative of a class of inputs. Thus, a more reliable similarity value can be obtained, using the strengths and weaknesses of the individual algorithms.

In a further embodiment, the further quantity is representative of a degree of similarity among the set containing the specific evolution and the further evolutions. Note that, in contrast with the preceding embodiment, there is no dichotomy here between the specific evolution and the further evolutions with regard to which is being compared to what in order to determine similarity. In this further embodiment, a degree of similarity is determined for the set containing the specific evolution and the further evolutions.

In a further embodiment of a method according to the invention, the further quantity is representative of a degree of similarity between the multiple further evolutions themselves. For example, the further quantity is representative of a mathematical function, e.g., an average, a mode, a median, of respective degrees of similarity between respective ones (2-tuples, 3-tuples) of the further evolutions. Note that only the multiple further evolutions in the neighborhood of the specific location eventually determine the allocation of the specific indicator to the specific location in the image, and that this embodiment does not consider the specific evolution at the specific location itself for determining the specific indicator to be allocated to the specific location.

In a further embodiment of the method, the specific neighborhood is configured to have at least one respective other one of the plurality of locations lying between the specific location and each respective one of the multiple further locations in the specific neighborhood. That is, the specific neighborhood does not include the locations immediately adjacent to the specific location.

For example, if the image is a 2-dimensional image, the multiple further locations may form a topological equivalent of an annulus whose inner perimeter encloses the specific location and the other locations. If each location is represented in the image as a pixel or a group of pixels, there lies at least one other pixel or one other group of pixels between, on the one hand, the pixel(s) representing the specific location and, on the other hand, any of the pixel(s) representing the multiple further locations taken into account for determining the further quantity. Likewise, if the image is a 3-dimensional image, the multiple further locations may form a topological equivalent of a shell, whose inner surface encloses the specific location and the other locations. If each location is represented in the image as a voxel (volumetric pixel) or a group of voxels, there lies at least one other voxel or one group of other voxels between, on the one hand, the voxel(s) of the specific location and, on the other hand, any of the further voxels representing the multiple further locations taken into account for determining the further quantity. That is, the further quantity is determined for a specific location (e.g., of a pixel, or of a voxel) with reference to multiple further locations (further pixels, further voxels) at a certain distance from the specific location that is larger than the distance between adjacent locations.

An advantage of this approach is the following. Noise in the evolution as determined at the specific location (e.g., the specific pixel) and noise in the evolution as determined at an adjacent location (e.g., a pixel adjacent to the specific pixel) are typically correlated. For example, the resolution of an image obtained through conventional medical imaging techniques turns out, in practice, to be higher than the physical resolution of the scanner used in this imaging technique. This results from some interpolation algorithm being applied in the scanner proper. Noise correlation in neighboring pixels can also be due to pre-processing techniques implemented by the scanner in order to enhance image quality, e.g., by means of image filtering techniques. Accordingly, neighboring pixels in the image are just the result of this interpolation and/or additional pre-processing techniques applied to the image and have similar noise characteristics. The inventor therefore proposes to ignore the immediately adjacent locations and to take into account the locations in the neighborhood of the specific location that lie at a distance from the specific location. The distance is chosen in dependence on the physical resolution of the scanner and is still higher than that, which is necessary to detect a clinically significant tumor (0.5 cm for prostate cancer, for example).

For a similar reason, the specific neighborhood may, as an option, be designed so as to be composed only of multiple further pixels that are not immediately adjacent to one another.

In a further embodiment, the further quantity is representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations. For example, the first group contains further evolutions associated with further locations nearer to the specific location and the second group contains the further evolutions associated with further locations farther from the specific location. As another example, the first group contains further evolutions associated with further locations nearer to the specific location as well as the specific evolution at the specific location, whereas the second group contains the further evolutions associated with further locations farther from the specific location.

The specific neighborhood of the specific location determines the further evolutions taken into account when determining the further quantity. The specific neighborhood may have isotropic, uniform spatial characteristics. For example, the specific neighborhood in a two-dimensional scenario forms a circular ring of uniform thickness or a square with uniform thickness, with the specific location at its center. As another example, the specific neighborhood in a three-dimensional scenario forms a spherical shell of uniform thickness or a cube of uniform thickness, with the specific location at its center. A spatially uniform neighborhood is used, for example, in case the operation of determining the further evolutions at the further locations of the neighborhood is independent on the whereabouts of the further locations with respect to the perfusable structure. The scanner used for tracing the spatial density of the traceable agent throughout the perfusable structure has a uniform resolution independent of the position of the location being scanned.

Alternatively, the specific neighborhood is configured to have non-uniform spatial characteristics. This non-uniformity may come into play if, for example, the scanner used for tracing the spatial density of the traceable agent throughout the perfusable structure provides an output that is inherently asymmetric with regard to spatial characteristics. As an example, an ultrasound scanner has typically a longitudinal resolution that is higher than the lateral resolution. The neighborhood could therefore have an asymmetry with respect to the specific location in order to take this anisotropic resolution into account. For example, the specific neighborhood may have non-uniform width. For example, the number of further locations between, on the one hand, the inner perimeter or inner surface of the specific neighborhood and, on the other hand, the outer perimeter or outer surface of the specific neighborhood is non-uniform throughout the specific neighborhood. As another example, some of the further locations on the inner perimeter or inner surface of the specific neighborhood lie substantially closer to the specific location than other ones of the further locations on the inner perimeter or inner surface of the specific neighborhood. For example, if the specific neighborhood is shaped as a square, the specific location may lie closer to one of the inner sides of the square than to the opposing one of the inner side. As yet another example, both the width of the specific neighborhood and the distance from the specific location to the inner perimeter or inner surface may vary.

Above paragraphs specify briefly the invention exploited as a method to control generating an image, e.g., providing the indicators per location in order to enable someone else to generate an image, or generating the image under control of the indicators determined.

The invention can also be exploited as a system for controlling generating an image of a perfusable structure of an organism. A fluid is flowing through the perfusable structure, and a dose of a traceable agent is present in the fluid flowing through the perfusable structure. The system comprises an input for receiving a multitude of samples. Each respective particular one of the samples is indicative of a physical quantity, representative of a spatial concentration of the traceable agent at a particular one of a plurality of locations in the perfusable structure at a respective time of sampling. In operational use of the system, the system is connected to an output of a scanner that produces the samples, e.g., a scanner of a type such as used in a perfusion scanning medical imaging technique. Alternatively, the system itself includes such a scanner. The system also comprises a memory for storing the samples, and a data processing sub-system connected to the memory. The data processing sub-system is configured for carrying out operations for each specific one of the plurality of locations in the perfusable structure. The operations comprise: determining a further quantity dependent on multiple further evolutions of the physical quantity, wherein each respective one of the multiple further evolutions is determined for a respective one of multiple further ones of the plurality of locations in a specific neighborhood of the specific location; and allocating a specific indicator to the specific location in dependence on the further quantity for control of representing the specific location in the image.

The system of the invention is configured to provide the specific indicators to control representing the specific locations in an image. The specific indicators may be stored in a memory for use later on, e.g., as data for being rendered as an image on a display monitor or for being printed. The image indicates the specific locations under control of the specific indicators, or for adding the representations of the specific locations to an existing image. Alternatively, the specific indicators may be supplied to a display monitor or to another image generation unit for controlling the generation of the image substantially in real-time with the scanning operation.

In an embodiment of a system in the invention, the operations comprise determining a specific evolution of the physical quantity at the specific location; and the further quantity is representative of a degree of similarity of the specific evolution to the multiple further evolutions. For example, the physical quantity is a result of comparing the specific evolution at the specific location to the further evolutions in the specific neighborhood of the specific location. The result of the comparison determines the specific indicator.

In a further embodiment of a system in the invention, the further quantity is representative of a degree of similarity between the multiple further evolutions themselves. Now, the specific indicator is determined by an attribute of the further evolutions in the specific neighborhood, and does not take into account the specific evolution at the specific location itself.

In a further embodiment of a system in the invention, the specific neighborhood is configured to have at least one respective other one of the plurality of locations lying between the specific location and each respective one of the multiple further locations in the specific neighborhood. For example, the specific neighborhood is topologically equivalent to an annulus enclosing the specific location, if the image is a 2-dimensional image. As another example, the specific neighborhood is topologically equivalent to a shell enclosing the specific location, if the image is a 3-dimensional image. Advantages of these features have been discussed above.

In a further embodiment of the system in the invention, the further quantity is representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations. For example, the first group contains further evolutions associated with further locations nearer to the specific location and the second group contains the further evolutions associated with further locations farther from the specific location. As another example, the first group contains further evolutions associated with further locations nearer to the specific location as well as the specific evolution at the specific location, whereas the second group contains the further evolutions associated with further locations farther from the specific location.

In a further embodiment of a system according to the invention, the specific neighborhood is configured to have different spatial properties in different directions with reference to the specific location. A context for considering anisotropic spatial properties of the specific neighborhood has been given above.

The invention can also be exploited as control software on a computer-readable medium. The control software is configured for control of generating an image of a perfusable structure of an organism, e.g., on display monitor or on a print-out from a printer, etc. A fluid is flowing through the perfusable structure, and a dose of a traceable agent is present in the fluid flowing through the perfusable structure. The control software is configured for operating on a multitude of samples. Each respective particular one of the samples is indicative of a physical quantity, representative of a spatial concentration of the traceable agent at a particular one of a plurality of locations in the perfusable structure at a respective time of sampling. The control software comprises first instructions for determining, for each specific one of the plurality of locations in the perfusable structure, a further quantity dependent on multiple further evolutions of the physical quantity, wherein each respective one of the multiple further evolutions is determined for a respective one of multiple further ones of the plurality of locations in a specific neighborhood of the specific location. The control software comprises second instructions for allocating, to each specific one of the plurality of locations in the perfusable structure, a specific indicator in dependence on the further quantity for control of representing the specific location in the image.

Such control software can be used, e.g., to render a general-purpose computer suitable for carrying out the method of the invention. Alternatively, the control software is a special component for use in a dedicated system for controlling the generation of the image.

In an embodiment of the control software, the control software comprises third instructions for determining, for each specific (108) one of the plurality of locations in the perfusable structure, a specific evolution of the physical quantity at the specific location. The further quantity is representative of a degree of similarity of the specific evolution to the multiple further evolutions.

In a further embodiment of the control software in the invention, the further quantity is representative of a degree of similarity between the multiple further evolutions themselves.

In a further embodiment of the control software in the invention, the specific neighborhood is configured to have at least one respective other one of the plurality of locations lying between the specific location and each respective one of the multiple further locations in the specific neighborhood. For example, the specific neighborhood is topologically equivalent to an annulus enclosing the specific location, if the image is a 2-dimensional image. As another example, the specific neighborhood is topologically equivalent to a shell enclosing the specific location, if the image is a 3-dimensional image.

In a further embodiment of the control software according to the invention, the further quantity is representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations. For example, the first group contains further evolutions associated with further locations nearer to the specific location and the second group contains the further evolutions associated with further locations farther from the specific location. As another example, the first group contains further evolutions associated with further locations nearer to the specific location as well as the specific evolution at the specific location, whereas the second group contains the further evolutions associated with further locations farther from the specific location.

In a further embodiment of the control software in the invention, the specific neighborhood is configured to have different spatial properties in different directions with reference to the specific location.

BRIEF DESCRIPTION OF THE DRAWING

The invention is explained in further detail, by way of example and with reference to the accompanying drawing, wherein.

Throughout the Figures, similar or corresponding features are indicated by same reference numerals.

DETAILED EMBODIMENTS

The invention relates to using a perfusion scanning medical imaging technique to generate an image of a perfusable structure of an organism. A fluid is flowing through the structure, and a dose of a traceable agent has been introduced into the fluid, or generated within the fluid. The evolution of the spatial concentration of the agent, e.g., a set of values of the magnitude of the concentration assumed at various moments over a period of time, is determined for a plurality of locations within the structure. The spatial pattern of the evolutions is analyzed and an image is generated on the basis of this analysis in order to enable the medical practitioner to draw conclusions about the dispersion characteristics of the perfusable structure.

Figure 1:
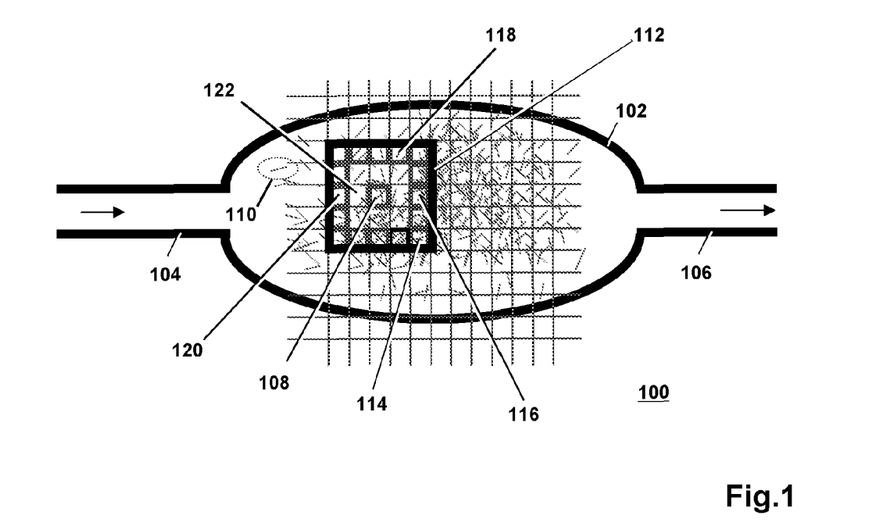
FIGS. 1, 2, 3, 4 and 5 are schematic diagrams of a perfusable structure.

FIG. 1 is a schematic image 100 of a perfusable structure 102 of an organism, e.g., a gland such as the prostate in a male mammal. The main blood supply to the prostate is provided by the internal iliac arteries. These internal iliac arteries branch from a pair of common iliac arteries, each perfusing one of the legs. The internal iliac arteries perfuse the prostate via the pudendal arteries, and terminate into the inferior vesical arteries. Additional perfusing is provided by branches of the superior and middle rectal arteries. The image 100 of the prostate 102 schematically represents the prostatic blood supply from an entrance 104 via the prostate 102 to an exit 106.

A tumor (neoplasm) is composed of fast growing tissue. The tumor needs a proper blood supply in order to receive the required amounts of oxygen and nutrients. It is widely recognized that once a tumor reaches a certain size, it requires its own blood supply and induces the development of new blood vessels (neovascularization). For more background see, e.g., J. Folkman et al., Nature, Vol. 339, pp 58-61, 1989; and N. Weidner et al., N. Engl. J. Med., Vol. 324(1) pp 1-8, 1991. This size limit is about 1 mm3.

Tumor-induced neovascularization can be quantified by the microvascular density (MVD), i.e., the number of microvessels per unit area. A small part of a tissue may be surgically removed from a patient for being examined. A pathologist cuts the part into thin slices and counts the vessels by analyzing the surface of such slices. Specific markers are used to highlight the vessels. The microvascular density is then characterized by the number of vessels per unit area of the surface of a slice. At the site of a tumor, MVD can be several times higher than the density of healthy tissue see, e.g., S. A. Bigler et al., Hum. Pathol. Vol. 24, pp. 220-226, 1993.

The invention uses a perfusion scanning medical imaging technique in order to examine the flow of blood (hemodynamic analysis) for extracting hemodynamic parameters which are typically related to the presence of a tumor. A traceable agent, introduced into the blood flow, enables to track the blood flow. In the invention, the temporal characteristics are determined of the dispersion of the traceable agent at a plurality of locations throughout the prostate 102.

The evolution (i.e., the dynamics) of the dispersion of the traceable agent as monitored at different locations throughout the prostate 102, allows drawing conclusions about the character of the vascular structure of the prostate. For example, a higher rate of diffusion (intravascular dispersion dynamics) of the traceable agent corresponds to a higher degree of similarity between the evolutions monitored at neighboring locations. A higher rate of diffusion may, therefore, correspond to a higher spatial density of blood vessels. As mentioned earlier, as convection plays a relevant role, the degree of similarity will also correlate with the ratio of the transport of the traceable agent by means of convection and the transport of the traceable agent through dispersion. The degree of dispersion, also relative to convection and, therefore, the degree of similarity can be associated with the underlying microvascular structure and can thus be used to characterize the presence of angiogenesis. Angiogenesis can be a symptom of the presence of cancer or other forms of tissue inflammation.

Consider the scenario wherein the blood is flowing through the prostate 102 in the direction of the arrows, i.e., from the entrance 104 to the exit 106, and wherein a dose of a traceable agent has been introduced into the blood upstream of the entrance 104. Further, consider a 2-dimensional imaging technique, wherein the image 100 produced is a 2-dimensional image of the prostate 102.

In the imaging technique the dispersion of the traceable agent is monitored over the prostate 102. As the traceable agent is being distributed over the prostate 102 via the prostatic vascular system, monitoring the traceable agent enables to chart the prostatic blood vessels in the image 100. The presence of the traceable agent at a specific location in the prostate 102 is represented in the image 100 of the prostate 102 as a graphical feature, whose position in the image 100, e.g., position 108, corresponds with the specific location of the traceable agent in the prostate 102 and which contrasts with the background. The spatial density of the features at the corresponding position 108 in the image 100 increases with the spatial concentration of the traceable agent at the specific location. The features are graphically represented by grey lines. In order to not obscure the drawing, a single one of such features is indicated with reference numeral 110.

For convenience, the entity "position in the image 100" will be referred to herein below as "pixel". It is clear that the entity "a position in the image 100" can similarly be represented by a group of pixels that together cover an area bounded by a closed curve. Accordingly, a particular location in the prostate 102 corresponds to a particular pixel in the image 100. For the sake of clarity, the diagram of the image 100 shows the pixels as being of uniform shape, here: a square, and organized in a rectangular grid of rows and columns. Depending on the imaging technique used, the pixels need neither be uniformly shaped, nor square, nor organized in a rectangular grid. For example, the scanner used in the imaging technique to capture the 2-dimensional image may have a directional sensitivity, and the resulting image may be a geometrically distorted representation of reality, e.g., the representation is elongated in a pre-determined direction with respect to reality.

An embodiment of a method according to the invention now proceeds as follows. For each specific one of a plurality of locations in the prostate 102, e.g., the location corresponding with a specific pixel 108, a specific evolution is determined of a physical quantity that is representative of a spatial concentration of the traceable agent at the specific location. As mentioned above, the term "evolution" is indicative of the dynamics of the dispersion, the way, wherein the concentration of the traceable agent changes over time at the specific location. Accordingly, the evolution is determined individually for each individual specific location. Then, for each specific location, the evolution, as determined for this specific location, is compared to a quantity that is indicative of the evolution at other locations in its neighborhood. For example, the comparison may be carried out by means of quantifying the respective similarity between the evolution at the specific location and the evolution of each respective one of the neighboring locations, and processing the quantified similarities of the individual comparisons so as to come up with a single measure of similarity to be assigned to the specific location, e.g., by averaging the respective quantified similarities, the averaging using a uniform weighting factor of unity for each quantified similarity or different weighting factors. Alternatively, the comparison is carried out by first averaging the evolutions at the neighboring locations and quantifying the similarity between, on the one hand, the evolution determined at the specific location and, on the other hand, the evolution, averaged over the neighborhood.

In the diagram of FIG. 1, the image 100 of the prostate 102 is composed of a plurality of pixels. Only some of the pixels are individually indicated with reference numerals in order to not obscure the drawing. At each specific location, e.g., the specific location corresponding to the specific pixel 108, a similarity value is determined between the evolution of the spatial concentration of the traceable agent, and the evolution in a specific neighborhood of the specific location. In the image 100, the specific neighborhood of the specific location corresponds with a specific region 112 enclosing the specific pixel 108. The outer perimeter of the specific region 112 defines a square, and is indicated with wide black line segments. The specific region 112 consists of multiple further pixels, of which only a few have been individually indicated in order to not obscure the drawing: e.g., a first further pixel 114, a second further pixel 116, a third further pixel 118, and a fourth further pixel 120. The further pixels form a closed band that is centered on the specific pixel 108 and that has a uniform width of a single pixel.

In the example shown, at least one other pixel is present between the specific pixel 108 and any of the further pixels of the specific region 112. For example, the specific pixel 108 is separated from the fourth further pixel 120 by another pixel 122. As explained above, a reason for having a distance between the specific pixel 108 and the further pixels of the region 112 is the following. A degree of similarity is determined between, on the one hand, the evolution at the specific location corresponding to the specific pixel 108 and, on the other hand, the evolution in the specific neighborhood of the specific location, the specific neighborhood corresponding to the specific region 112. The degree of similarity is quantified in a parameter value assigned to the specific pixel. In order to reduce the effect of noise occurring in neighboring pixels of the image 100 as a result of an interpolation procedure applied in the imaging technique of the scanner, it is advantageous to have a spatial separation between the specific location, corresponding to the specific pixel 108, and the further locations in the specific neighborhood, corresponding to the further pixels in the specific region 112. As mentioned earlier, the specific neighborhood 112 may be shaped by selecting suitable weighting factors for combining the evolutions of the further locations in the neighborhood 112.

The specific pixel 108 and the specific region 112 have been indicated in the diagram of FIG. 1 to illustrate a single procedure to determine a similarity value for the specific pixel 108.

Figure 2:
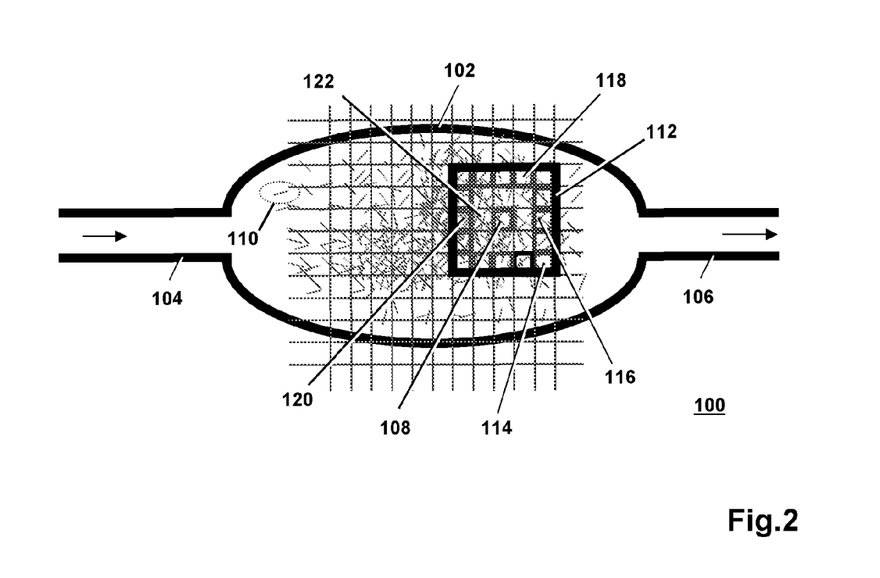

The grid has a plurality of pixels arranged in rows and columns. Each particular one of the pixels in the grid covering the image's area of interest becomes "the specific pixel" in above terminology when the associated similarity value is to be determined for that particular pixel with reference to the specific region centered on the particular pixel. This is illustrated in FIG. 2 wherein the similarity value is to be determined for a new specific pixel 108. The reference numerals of the diagram of FIG. 1 have been maintained.

In the diagrams of FIGS. 1 and 2, the specific region 112 has been illustrated as having symmetrical spatial properties, i.e., a square band of uniform width and centered on the specific pixel 108.

Figure 3:
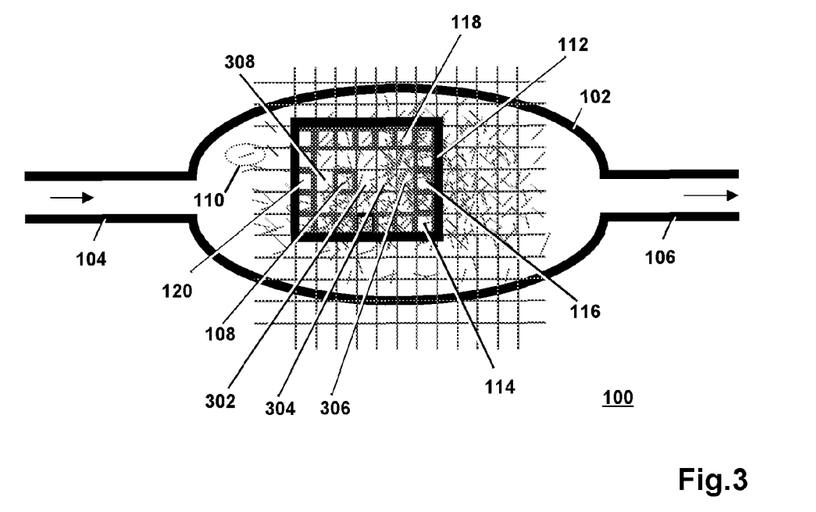
Figure 4:
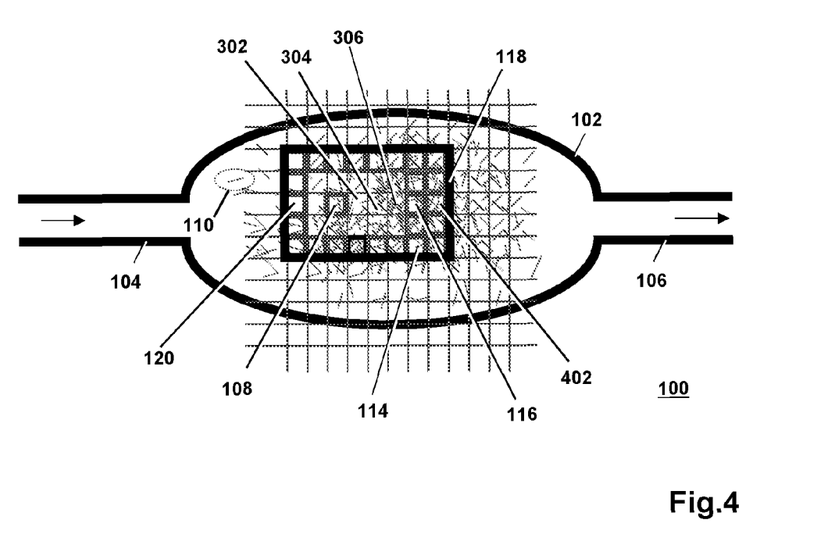

The diagrams of FIGS. 3 and 4 illustrate examples, wherein the specific region 112 is chosen to have asymmetrical properties. In the diagram of FIG. 3, the specific region 112 has a rectangular outer perimeter with sides of different length. Optionally, the specific region 112 is not centered on the specific pixel 108. Now, the specific pixel 108 and the second further pixel 116 are separated by three other pixels, to with a first other pixel 302, a second other pixel 304, and a third other pixel 306, whereas the specific pixel 108 and the fourth further pixel 120 are separated by a single other pixel, to wit a fourth other pixel 308. In the diagram of FIG. 4, the specific region 112 is chosen to have a non-square rectangular outer perimeter, as in the diagram of FIG. 3, and not-centered on the specific pixel 108, as in the diagram of FIG. 3. In addition, the specific region 112 in the diagram of FIG. 4 is a band of non-uniform width. More specifically for this example: on the right-hand side of the specific pixel 108 the specific region 112 is two pixels wide, e.g., the second further pixel 116 and a fifth further pixel 402, whereas on the left-hand side of the specific pixel 108 the specific region 112 has a width of a single pixel see, e.g., the fourth further pixel 120.

Above examples illustrate the spatial character (e.g., the size and shape of the inner perimeter and the outer perimeter) of the specific region 112 taken into account when determining the similarity value to be assigned to the specific pixel 108.

Figure 5:
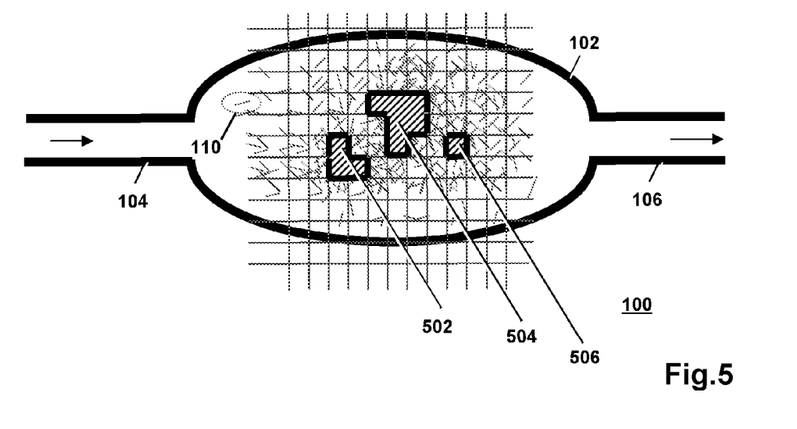

As mentioned before, all pixels in the area of interest are being processed as described above for the specific pixel 108. The result of this processing is a set of similarity values, each respective one thereof being associated with a respective one of the pixels considered. The set of similarity values are now used to determine individual indicators, each respective one associated with a respective one of the pixels considered, that control the visual representations of the locations of the prostate 102 in the image 100. For example, the similarity values obtained are mapped onto the real numbers in a predetermined range, and the range is divided into a number of intervals. If a particular similarity value is mapped into a particular interval, the particular pixel associated with the particular similarity value is given a particular intensity, or a particular color, or particular shading, etc. In the diagram of FIG. 5, for example, a similarity values is mapped onto zero if the similarity is below a certain threshold, and else onto unity. Pixels with a similarity value mapped onto zero do not receive a visual indicator, whereas pixels mapped onto unity do receive a separate visual indicator, here a type of shading. Accordingly, the pixels with high similarity values are indicated in the diagram of FIG. 5 as a first patch 502, a second patch 504 and a sixth patch 506.

As another example, the arrangement of the pixels considered and the similarity values obtained define a mapping of a part of a two-dimensional plane ($\mathcal{R}^2$, the X-Y-plane) onto the real axis ($\mathcal{R}$). The mapping can be visualized in three dimensions ($\mathcal{R}^3$) as a two-dimensional surface, wherein the X-coordinate and the Y-coordinate of a particular position on the surface are indicative of the position of a particular pixel in the image 100, and wherein the Z-coordinate is indicative of the particular similarity value obtained for the particular pixel.

Above is an example, wherein the field of similarity values themselves is directly mapped to a graphical indicator. As an alternative, the magnitudes of the gradient of the similarity values or any other field, obtained by subjecting the field of similarity values to suitable vector operations, is mapped to graphical indicators. That is, the similarity values obtained are pre-processed before creating visual indicators in the image of the locations in the prostate that are of interest. Pre-processing operations can also include statistical analysis of the spatial distribution of the similarity values for extracting local parameters indicating, for example, the local variance or the standard deviation of the similarity values obtained. By means of choosing different pre-processing operations different features can be highlighted in the image.

Figure 6:
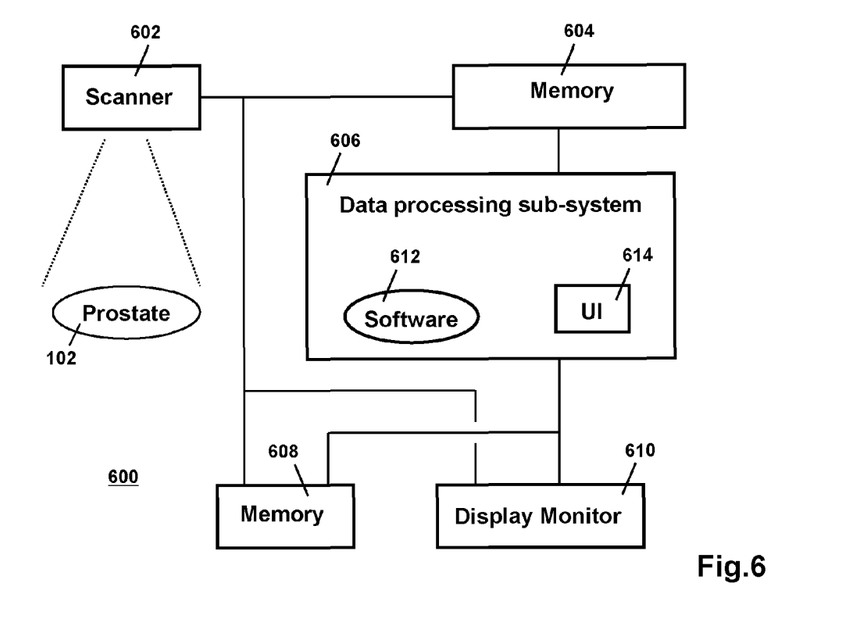
FIG. 6 is a block diagram of a system in the invention.

FIG. 6 is a diagram of a system 600 in the invention. The system 600 is configured for controlling generating the image 100 of the prostate 102. The system 600 comprises a scanner 602 for scanning the prostate 102 while the blood that is flowing through the prostate 102 is dispersing a traceable agent throughout the prostate 102. The scanner 602 is producing specific data samples for each specific one of a plurality of locations in the prostate 102. Each respective, particular sample is indicative of e.g., the spatial concentration of the traceable agent at a particular location in the perfusable structure at a respective time of sampling. Such a scanner 602 is well known in the art of perfusion scanning medical imaging techniques, and will not be discussed in further detail. The system 600 comprises a first memory 604 configured for buffering the specific data samples for each location. The system 600 further has a data processing sub-system 606. The data processing sub-system 606 is connected to the first memory 604 for receipt of the samples. The data processing sub-system 606 is configured for subjecting the samples to operations for each specific location in the prostate 102. The data processing sub-system 606 determines the evolution of the spatial concentration of the traceable agent for each of the locations in the prostate 102. The data processing sub-system 606 then determines for each specific evolution a specific similarity value. As discussed above, the specific similarity value is representative of a similarity of the specific evolution to a further quantity that is indicative of multiple further evolutions of the physical quantity, wherein each respective one of the multiple further evolutions is determined for a respective one of multiple further ones of the plurality of locations in a specific neighborhood of the specific location. The data processing sub-system 606 also generates a specific indicator for being allocated to the specific location in dependence on the specific similarity value. The specific indicator controls representing the specific location in the image 100, e.g., by means of controlling a visual attribute (e.g., color, intensity, shading, etc.) of the specific pixel 108, in the image 100. The indicators produced for all locations in the prostate 102 can, for example, be stored in a second memory 608, together with the specific data samples received from the scanner 602 and/or information on the corresponding evolutions, for later use. Alternatively, the specific indicators produced for all locations in the prostate 102 and the specific data samples received from the scanner 602 are supplied to a display monitor for rendering the specific data samples as well as the specific indicators. As has been explained above, the data processing sub-system 606 requires data samples of the specific neighborhood 112 in order to generate the specific indicator associated with the specific location 108 in the prostate 102. As a result, the process of generating the specific indicator can only start after the data samples representative of the specific location 108 in the prostate 102 and of the specific neighborhood 112 have become available. Accordingly, generating a time sequence of images 100 at the display monitor 610 in substantially real-time requires that the supply of the specific data samples from the scanner 602 be shifted in time to have them synchronized with the availability of the specific indicators.

The data processing sub-system 606 may be a dedicated data processing unit or a generic computer running dedicated software stored on a computer-readable medium 612 and configured for controlling carrying out the method of the invention. The data processing sub-system 606 may have a user-interface 614 for enabling the operator to control the data processing, e.g., to enable selection of one of a plurality of different algorithms (e.g., an algorithm based on coherence, an algorithm based on correlation or an algorithm based on entropy, or a specific algorithm that is based on one of coherence correlation and entropy, and that uses one or more specific parameter values), or parameter settings (e.g., the further locations in the neighborhood 112 and their relative weighting factors for weighting the further evolutions) for determining the degree of similarity, to enable selection of one of a plurality of algorithms to pre-process the similarity values for mapping the preprocessed similarity values onto the visual indicators, etc.

Figure 7:
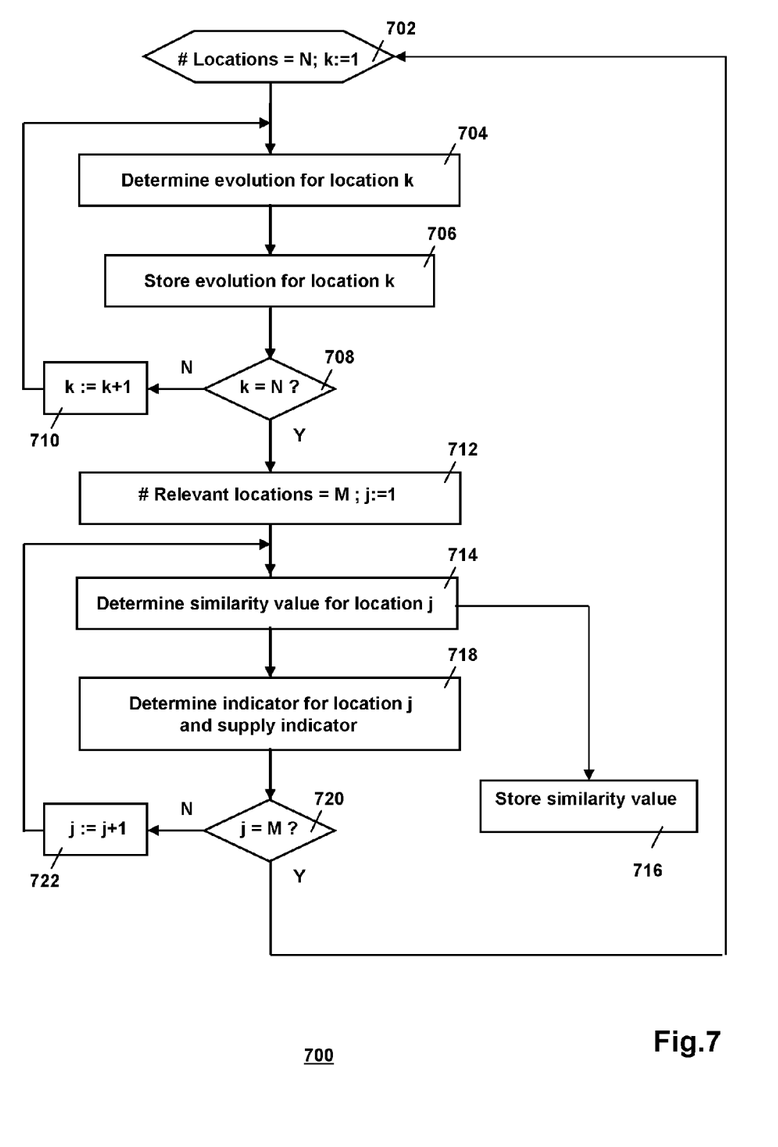
FIGS. 7 and 8 are process diagrams of processes in the invention.

FIG. 7 is a flow diagram of a process 700 in a method according to the invention. The process 700 starts in a first step 702, wherein it is determined the prostate 102 is going to be scanned at a number of N locations in the prostate 102. Each individual value of a running variable "k" indicates an individual one of the N locations. At the first step, the value of the running variable is set to unity.

In a second step 704, the evolution is determined for the location indicated by the current value of the running variable k.

In a third step 706, the evolution determined in the second step 704 is stored in a memory, e.g., in the first memory 604.

In a fourth step 708, it is determined whether or not the value of the running variable k has reached the value "N". If the running variable k has not yet reached the value "N", the process 700 proceeds with a fifth step 710, wherein the running variable k is incremented by unity, whereupon the process 700 returns to the second step 704. If the running variable k has reached the value "N", the process 700 proceeds with a sixth step 712.

In the sixth step 712, a number of relevant locations is set to "M", for which a similarity value is to be produced. The number M is necessarily equal or lower than the number N. If each location, for which a similarity value is to be determined, is to be evaluated with respect to a similarly shaped neighborhood, the number M is lower than N. This is a result of the fact that the locations on the very boundary of the scanned part of the prostate 102 are not embedded or completely enclosed within a full neighborhood. Each individual value of a running variable "j" indicates an individual one of the M locations. The running variable "j" is set to unity in the sixth step 712.

In a seventh step 714, the similarity value is determined for the location indicated by the current value of the running variable j.

In an (optional) eighth step 716, the similarity value determined in the seventh step 714 is stored, e.g., in the second memory 608.

In a ninth step 718, the indicator is generated for the location indicated by the current value of the running variable j, and supplied to, e.g., the second memory 608 or to the display monitor 610.

In a tenth step 720 it is determined whether or not the running variable j has reached the value "M". If the running variable j has not yet reached the value "M", the process 700 proceeds with an eleventh step 722, wherein the running variable j is incremented by unity, whereupon the process 700 returns to the seventh step 714. If the running variable j has reached the value "M", the process 700 ends or, as is shown in the flow diagram of FIG. 7, returns to the first step 702.

Figure 8:
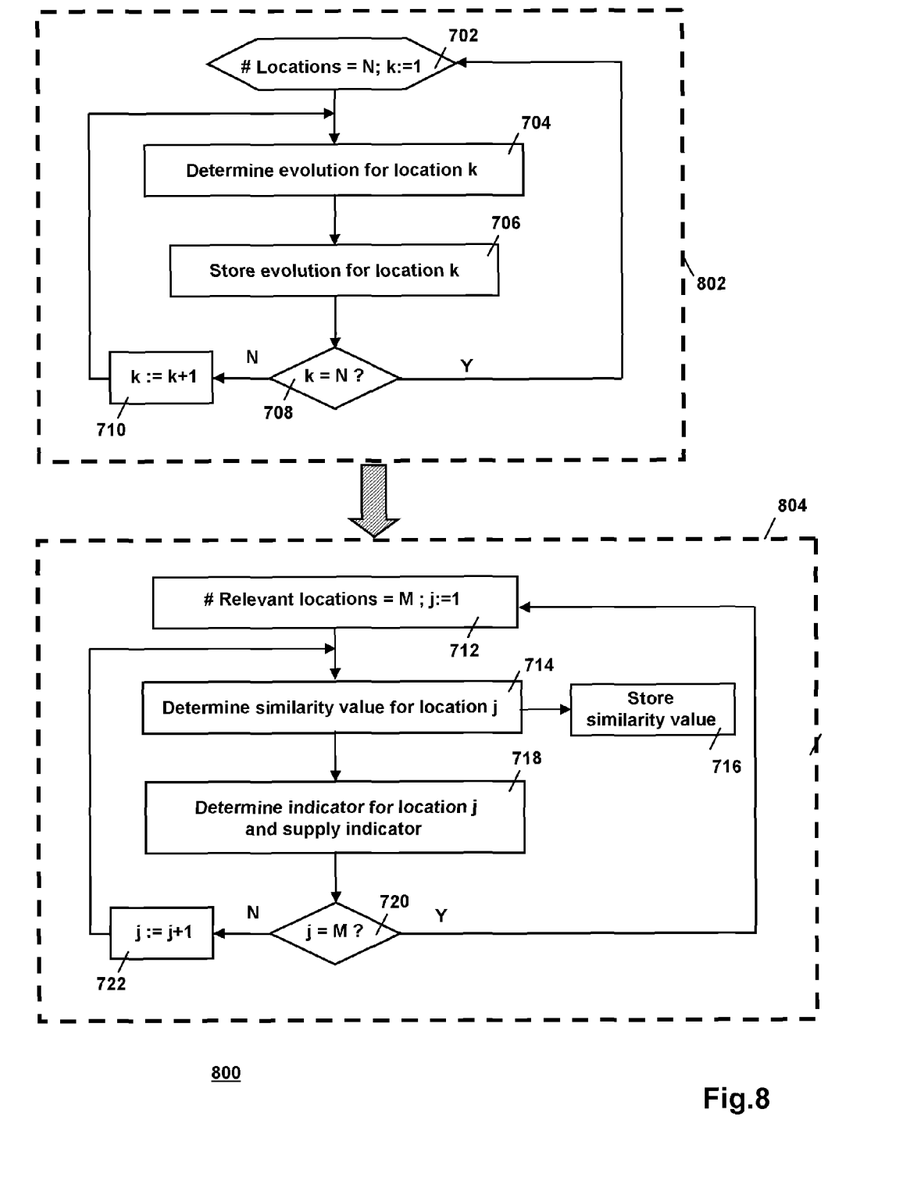

FIG. 8 is a diagram of an alternative process 800. In the alternative process 800, the first step 702, the second step 704, the third step 706, the fourth step 708 and the fifth step 710 together form a first subsidiary process 802; and the sixth step 712, the seventh step 714, the eighth step 716, the ninth step 718, the tenth step 720 and the eleventh step 722 form a second subsidiary process 804. The second subsidiary process 804 can start with determining the similarity value for a specific location, e.g., the specific location 108, as soon as the evolution at the specific location 108 and the evolutions at the further locations in the specific neighborhood 112 of the specific location 108 have been determined in the first subsidiary process 802. That is, the second subsidiary process 804 does not necessarily have to wait until the evolutions at all locations of the prostate 102 have been determined. Accordingly, some sort of pipeline processing can be adopted with the advantage of speeding up the data processing.

The examples discussed above with reference to FIGS. 1 to 8 specify that the specific indicator be produced on the basis of a degree of similarity between the evolution at the specific location and a further quantity representative of various further evolutions at further locations in the neighborhood of the specific location. As an alternative, the specific indicator is produced on the basis of a degree of similarity among the further evolutions only.

Figure 9:
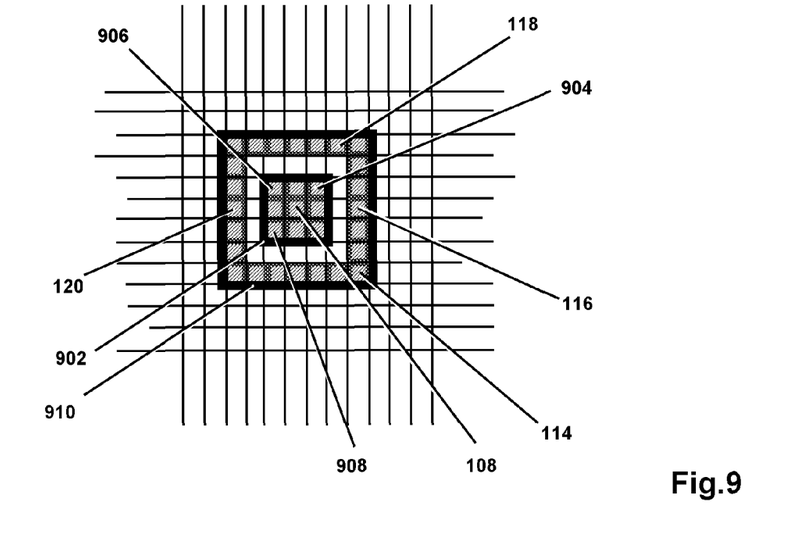
FIGS. 9 and 10 are diagrams illustrating examples of deriving a similarity measure.

FIG. 9 is a schematic diagram of a part of the image 100 of the prostate 102, illustrating a further variation on the theme of the invention. The further quantity, which is determined in dependence on multiple further evolutions of the spatial concentration of the traceable agent, is now representative of a similarity between groups of evolutions, each of the groups being associated with different regions of locations within the neighborhood 112 in the prostate 102. In the image 100, a first one of the groups 902 is formed by the locations that are represented in the image 100 as including the specific pixel 108 and multiple adjacent pixels in close vicinity of the specific pixel 108. In order to not obscure the drawing, only a first adjacent pixel 904, a second adjacent pixel 906 and a third adjacent pixel 908 are indicated in the diagram of FIG. 9. A second one of the groups 910 is formed by locations that lie on a band or a shell that surrounds the first group 902, here lying at a distance from the first group 902 and separated therefrom by a distance of a single location. The pixels associated with the first group 902 and with the second group 910 have been indicated by as hatched, i.e., marked with parallel lines lying close together. A measure of similarity is then obtained by comparing the evolutions of the first group 902 to the second group 910. For example, a first average evolution is determined for the locations of the first group 902, and a second average evolution is determined for the second group 910, and the similarity is based on comparing the first average to the second average. Other algorithms can be chosen to extract a similarity measure for interrelating the evolutions of the first group 902 and the evolutions of the second group 910, examples of which have been discussed above. As is clear, the diagram of FIG. 9 is only an example to illustrate generating a similarity measure by means of comparing different groups of evolutions. The spatial form of the first group 902 and the spatial form of the second group 910 can be chosen by the operator and need not be symmetrical. Similarly, the distance between the first group 902 and the second group 910 need not be uniform as in the diagram of FIG. 9, but may vary from location to location. Likewise, the second group 910 need not be one location wide, as in the diagram of FIG. 9, but may have a larger width. Similarly, each individual one of the hatched pixels of the first group 902 and/or the second group 910 need not be taken into account to determine the similarity between the evolutions of the first group and the evolutions of the second group. For example, the evolution associated with the specific pixel 108 may be ignored, so that only the evolutions associated with the adjacent pixels of the first group 902, including the first adjacent pixel 904, the second adjacent pixel 906 and the third adjacent pixel 908, are taken into consideration. More generally, the further quantity may be representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations. The first group may, but need not, include the specific evolution.

Figure 10:
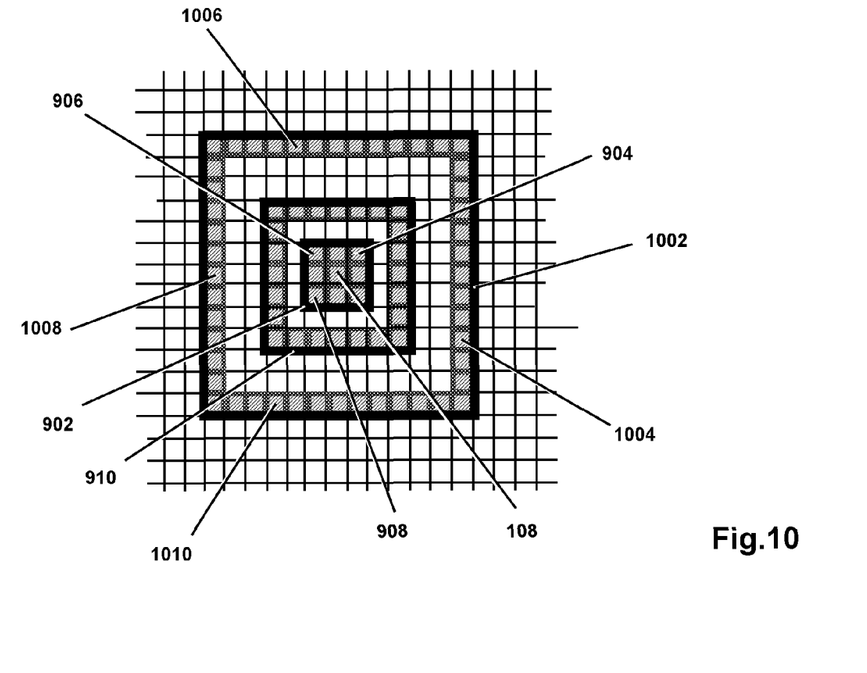

FIG. 10 is a schematic diagram of a part of the image 100 of the prostate 102, illustrating another variation on the theme of the invention. The further quantity, which is determined in dependence on multiple further evolutions of the spatial concentration of the traceable agent, is now representative of a measure of similarity derived from more than two groups of evolutions. In the example shown in the schematic diagram of FIG. 10, the further evolutions that are taken into account for determining the further quantity are associated with multiple groups of further locations, to wit: the further evolutions at the further locations of the first group 902, the further evolutions at the further locations of the second group 910, and the further evolutions at the further locations of a third group 1002. Of the third group 1002 of further locations, only a fifth further location 1004, a sixth further location 1006, a seventh further location 1008 and an eighth further location 1010 have been indicated with reference numerals in order to not obscure the drawing. In the 2-dimensional image 100, an individual one of the specific location and the further locations in the prostate 102 are represented as an individual pixel, or as an individual group of pixels. The concepts "location in the prostate 102" and "pixel in the image 100 of the prostate 102" are used interchangeably in this text if there is no reason for confusion.

Accordingly, the further evolutions considered are taken from different groups of locations, wherein the next one of the groups forms part of a region that encloses the previous one(s) of the groups. In the 2-dimensional example of the diagram of FIG. 10, the third group 1002 is included in a region that topologically forms an annulus, which encloses the second group 910. The second group 910 is included in a region that, in a topological sense, forms an annulus enclosing the first group 902. The 3-dimensional equivalent would topologically be a hierarchy of nested shells.

As in clear, more than three groups of further locations can be used, wherein each of the groups is included in a region that encloses or encompasses the groups of locations closer to the specific location.

When determining the further quantity, e.g., a similarity measure, the further evolutions of the first group 902 may be given weighting factors of higher magnitude than the further evolutions of the second group 910, and the magnitude of the weighting factors of the further evolutions in the second group 910 may, in turn, be higher than the magnitude of the weighting factors of the further evolutions of the third group 910, and so on.

The invention claimed is:

1. A method of controlling generating an image of a perfusable structured of an organism, wherein:
   a fluid is flowing through the perfusable structure;
   a dose of a traceable agent is present in the fluid; and wherein
   for each specific one of a plurality of locations in the perfusable structure, the method comprises:
   determining multiple further evolutions of a physical quantity, representative of a spatial concentration of the traceable agent, wherein each respective one of the multiple further evolutions is determined for a respective one of multiple further ones of the plurality of locations in a specific neighborhood of the specific location;
   optionally, determining a specific evolution of the physical quantity at the specific location;
   determining a further quantity dependent on a degree of similarity between the multiple further evolutions themselves, or on a degree of similarity of the specific evolution to the multiple further evolutions, and
   allocating a specific indicator to the specific location in dependence on the further quantity for control of representing the specific location in the image.

2. The method of claim 1, wherein the specific neighborhood is configured to have at least one respective other one of the plurality of locations lying between the specific location and each respective one of the multiple further locations in the specific neighborhood.

3. The method of claim 1, wherein
   the further quantity is representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations.

4. The method of claim 1, wherein the specific neighborhood is configured to have different spatial properties in different directions with reference to the specific location.

5. A system for controlling generating an image of a perfusable structure of an organism, wherein:
   a fluid is flowing through the perfusable structure;
   a dose of a traceable agent is present in the fluid; and wherein
   the system comprises:
   an input for receiving a multitude of samples, wherein each respective particular one of the samples is indicative of a physical quantity representative of a spatial concentration of the traceable agent at a particular one of a plurality of locations in the perfusable structure at a respective time of sampling;
   a memory for storing the samples;
   a data processing sub-system connected to the memory and configured for carrying out operations for each specific one of the plurality of locations in the perfusable structure, wherein the operations comprise:
   (i) determining multiple further evolutions of the physical quantity, wherein each respective one of the multiple further evolutions is determined for a respective one of multiple further ones of the plurality of locations in a specific neighborhood of the specific location;
   (ii) optionally, determining a specific evolution of the physical quantity at the specific location;
   (iii) determining a further quantity dependent on a degree of similarity between the multiple further evolutions themselves, or on a degree of similarity of the specific evolution to the multiple further evolutions, and
   (iv) allocating a specific indicator to the specific location in dependence on the further quantity for control of representing the specific location in the image.

6. The system of claim 5, wherein the specific neighborhood is configured to have at least one respective other one of the plurality of locations lying between the specific location and each respective one of the multiple further locations in the specific neighborhood.

7. The system of claim 5, wherein the further quantity is representative of a degree of similarity between, on the one hand, a first group including respective first ones of the further evolutions that are associated with a first set of respective first ones of the further locations and, on the other hand, a second group of respective second ones of the further evolutions that are associated with a second set of respective second ones of the further locations.

8. A non-transitory computer readable medium embodying a computer program product comprising instructions for causing a processor system to perform a method according to claim 1.

* * * * *